(12) United States Patent
Andersson et al.

(10) Patent No.: US 11,714,091 B2
(45) Date of Patent: Aug. 1, 2023

(54) METHOD FOR ANALYZING THE 3D STRUCTURE OF BIOMOLECULES

(71) Applicants: Martin Andersson, Mölndal (SE); Mats Hulander, Gothenburg (SE); Gustav Sundell, Gothenburg (SE)

(72) Inventors: Martin Andersson, Mölndal (SE); Mats Hulander, Gothenburg (SE); Gustav Sundell, Gothenburg (SE)

(73) Assignee: Vitroprobe Analytics AB, Gothenburg (SE)

( * ) Notice: Subject to any disclaimer, the term of this patent is extended or adjusted under 35 U.S.C. 154(b) by 567 days.

(21) Appl. No.: 16/629,166

(22) PCT Filed: Jul. 4, 2018

(86) PCT No.: PCT/SE2018/050731
§ 371 (c)(1),
(2) Date: Jan. 7, 2020

(87) PCT Pub. No.: WO2019/013688
PCT Pub. Date: Jan. 17, 2019

(65) Prior Publication Data
US 2021/0364525 A1 Nov. 25, 2021

(30) Foreign Application Priority Data
Jul. 14, 2017 (SE) .................. 1750924-1

(51) Int. Cl.
*G01N 33/68* (2006.01)
*G01N 1/36* (2006.01)
(Continued)

(52) U.S. Cl.
CPC ......... *G01N 33/6803* (2013.01); *B81B 1/008* (2013.01); *G01N 1/36* (2013.01); *G01N 23/046* (2013.01)

(58) Field of Classification Search
CPC .................. G01N 23/046; G01N 33/6803
See application file for complete search history.

(56) References Cited

U.S. PATENT DOCUMENTS

| 6,303,290 B1 | 10/2001 | Liu et al. |
| 2003/0148291 A1 | 8/2003 | Robotti |
| 2007/0184515 A1* | 8/2007 | Goodman ............. H01J 37/285 435/40.5 |

FOREIGN PATENT DOCUMENTS

| EP | 2733730 A2 * | 5/2014 | ............. H01L 22/12 |
| WO | 2005026684 | 3/2005 | |
| WO | 2008057066 | 5/2008 | |

OTHER PUBLICATIONS

"Alkoxides," IUPAC. Compendium of Chemical Terminology, 2nd ed. (the "Gold Book"). Compiled by A. D. McNaught and A. Wilkinson. Blackwell Scientific Publications, Oxford (1997). doi:10. 1351/goldbook.A00225. Last revised: Feb. 24, 2014 (Year: 2014).*

(Continued)

*Primary Examiner* — Jennifer Wecker
*Assistant Examiner* — Michelle Adams
(74) *Attorney, Agent, or Firm* — Myers Bigel, P.A.

(57) ABSTRACT

The present invention relates to a method for determining the three dimensional structure of biomolecules, such as proteins, protein fragments, and peptides. The biomolecule is encapsulated in an amorphous silica matrix, from which a needle specimen is prepared. Atom probe tomography is then used to analyze the needle specimen and the data is used to reconstruct the three dimensional structure of the biomolecule. The present invention greatly facilitates determination of the three dimensional structure of biomolecules.

13 Claims, 9 Drawing Sheets

(51) Int. Cl.
  *G01N 23/046* (2018.01)
  *B81B 1/00* (2006.01)

(56) References Cited

OTHER PUBLICATIONS

Lagaly, G. et al. "Silicates," Ullmann's Encyclopedia of Industrial Chemistry: Wiley-VCH Verlag GmbH & Co. KGaA. (2012) pp. 509-572. (Year: 2021).*
Gruber, M. et al. "Laser-assisted atom probe analysis of sol-gel silica layers," Ultramicroscopy 109 (2009) 654-659 (Year: 2009).*
Bhatia et al. "Aqueous Sol-Gel Process for Protein Encapsulation" Chemistry of Materials, 12(8):2434-2441 (2000).
Bas et al. "A general protocol for the reconstruction of 3D atom probe data" Applied Surface Sciences, 87/88:298-304 (1995).
Bhatia et al. "Aqueous Sol-Gel Process for Protein Encapsulation" Chemistry of Materials, 12(8):2434-2441 (2000) (Abstract only).
Brinker, C.J. "Hydrolysis and Condensation of Silicates: Effects on Structure" Journal of Non-Crystalline Solids, 100:31-50 (1988).
Coradin et al. "Biogenic Silica Patterning: Simple Chemistry or Subtle Biology?" ChemBioChem, 3:1-9 (2003).
Geiser et al. "Wide-Field-of-View Atom Probe Reconstruction" Microscopy and Microanalysis, 15(S2):292-293 (2009).
Jackson et al. "Protein-Templated Biomimetic Silica Nanoparticles" Langmuir, 31(12):3687-3695 (2015).
Luckarift et al. "Enzyme immobilization in a biomimetic silica support" Nature Biotechnology, 22(2):211-213 (2004).
International Search Report and the Written Opinion of the International Searching Authority corresponding to International Patent Application No. PCT/SE2018/050731 (9 pages) (dated Oct. 5, 2018).

* cited by examiner

US 11,714,091 B2

METHOD FOR ANALYZING THE 3D STRUCTURE OF BIOMOLECULES

TECHNICAL FIELD

The present embodiments generally relate to analyzing three dimensional (3D) structures of biomolecules, and in particular to determining 3D structures of biomolecules using atom probe tomography.

BACKGROUND

The properties and biological function of a protein is intimately linked to its 3D structure. Knowledge of the 3D structure of a protein greatly increases the success in designing drugs, and in the field of pharmaceutical drug development, assessing the 3D structure of proteins is unquestionably the most important information in the quest for new therapeutic agents. Considerable effort is therefore invested in determining the 3D structure of these molecules to find or synthesize drugs with a desired pharmacological effect.

The two most common experimental techniques for protein structure determination are X-ray diffraction and nuclear magnetic resonance (NMR). In X-ray diffraction, proteins are purified and crystallized and subjected to an intense beam of X-rays, often originating from a synchrotron source. The diffracted X-rays will give a characteristic pattern of spots that is translated into the 3D-structure. In the best scenarios, the technique provides detailed structure information with atomic resolution of all atoms except hydrogen in the proteins and possible ligands present within the crystal. However, there are great limitations since not all proteins easily form crystals and relatively large sample volumes (about 2-10 $mm^3$) are needed to reach desirable signals. Especially transmembrane proteins have been shown difficult to crystallize. There are also limitations when studying flexible proteins and side chains, which often remains unseen. In addition, by crystallizing a protein, the topology of the protein may be distorted and the biologically active 3D structure incorrectly assessed.

The limitations of X-ray diffraction are to some extent complemented by NMR, where the local environment of atoms are analyzed when probed with a radio wave under the influence of a high magnetic field. The advantage of NMR is that proteins can be analyzed directly in liquid and that protein flexibility is of no concern. However, NMR suffers from time consuming and extensive computer calculations. Moreover, only small or medium-sized proteins may be examined due to overlapping peaks in the NMR spectra.

In addition to these techniques, electron microscopy (EM) techniques have been developed rapidly over the past decade to suit analyses of biological samples. In particular, cryo-electron microscopy/tomography have been employed. For cryogenic transmission electron microscopy (cryo-TEM) imaging, a hydrated sample is typically vitrified through flash-freezing in liquid ethane to prevent water crystallization and, hence, preserve the integrity of the protein. TEM images of ultra-thin slices of the sample are then taken from multiple angles and are later averaged and combined using image analysis to construct a 3D render of the protein. By using this approach 3D structures of proteins have been resolved with Angstrom resolution, although high resolution imaging is currently restricted to proteins larger than ~300 kDa. One limitation of EM for high resolution imaging and analysis of proteins is that no chemical information of the sample can be retrieved. In clear contrast, only the spatial distribution of the atoms in the sample is acquired.

There is therefore a need for efficient techniques for determining the 3D structures of biomolecules.

SUMMARY

It is a general objective to provide a method for determining the three dimensional structure of biomolecules.

This and other objectives are met by embodiments as disclosed herein.

An aspect of the embodiments relates to a method for determining a three dimensional (3D) structure of a biomolecule. The method comprises encapsulating the biomolecule in an amorphous silica matrix and preparing a needle specimen comprising the amorphous silica matrix. The method also comprises performing atom probe tomography analysis of the needle specimen to determine the 3D structure of the biomolecule.

The method of the present invention and the appended claims solves at least some of the above mentioned problems associated with determination of the 3D structure of biomolecules, such as proteins, fragments thereof, or peptides. This is achieved through embedding of the biomolecules into an amorphous silica matrix for further analysis with atom probe tomography (APT).

By embedding biological samples into an amorphous silica matrix, the present invention enables the fabrication of needle specimen tips with sufficient mechanical integrity to permit APT analysis of biomolecules with atomic resolution.

The present invention also solves a problem with background signal subtraction from the biological sample. By using an amorphous silica matrix, carbon species are easily distinguished from the background in the analyzed sample volume. This is in contrast to previous methods, where the sample tip is constructed of a (organic) polymer.

BRIEF DESCRIPTION OF THE DRAWINGS

The embodiments, together with further objects and advantages thereof, may best be understood by making reference to the following description taken together with the accompanying drawings, in which.

DESCRIPTION OF EMBODIMENTS

Figure 1:
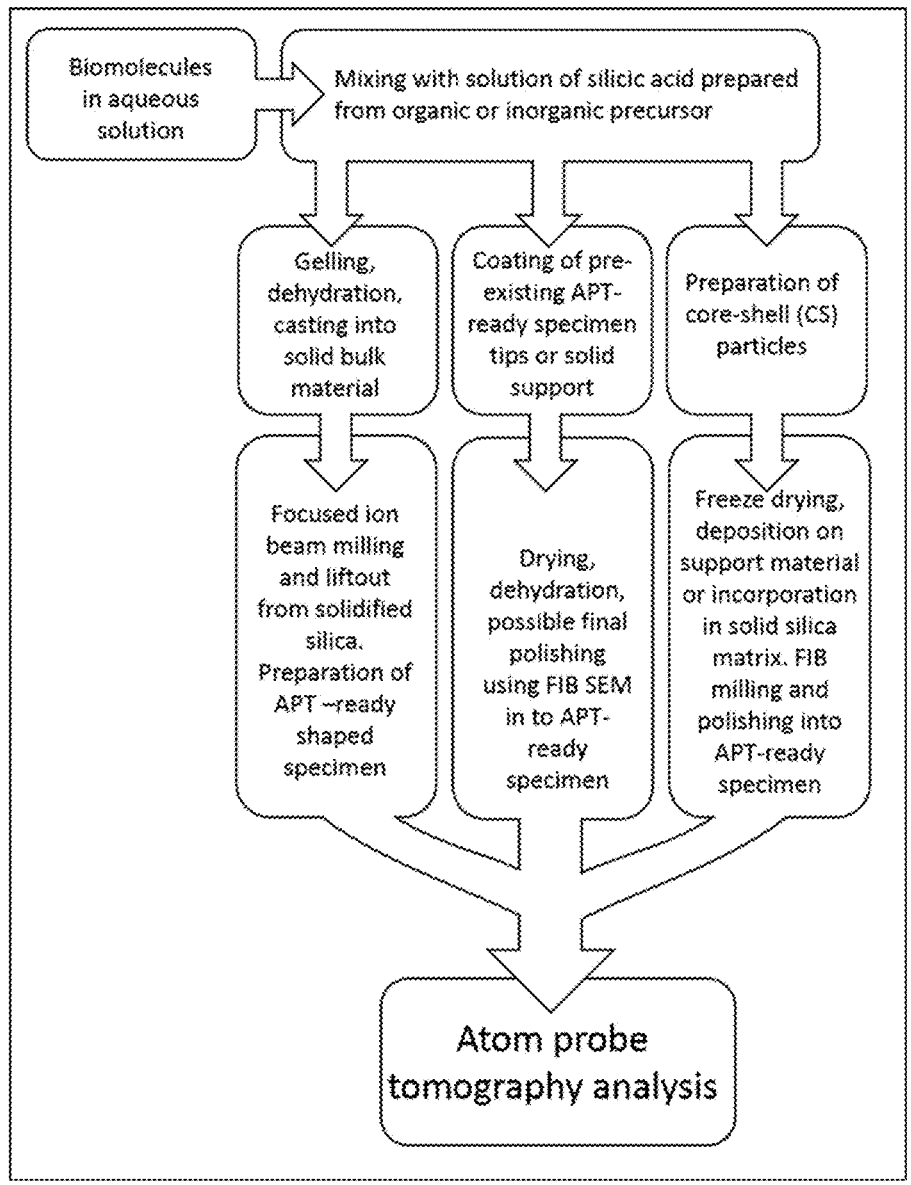
FIG. 1 is a flow chart that describing different embodiments of the invention, showing the processes from embedding of the biomolecule to analysis with atom probe tomography.

The present embodiments generally relate to analyzing three dimensional (3D) structures of biomolecules, and in particular to determining 3D structures of biomolecules using atom probe tomography.

Atom probe tomography (APT) is a powerful method in materials science, capable of chemical analysis in 3D on the sub-nanometer scale. The method is based on the ejection of atoms and molecules from the surface of a sharp needle-shaped specimen by the application of a large positive electric field. The electric field causes ionization of the atoms and molecules, whereby they are accelerated by the electric field toward a time-of-flight detector. As their time of flight is recorded and assembled in a mass spectrum, the chemical identity of each ion that reaches the detector can be evaluated. The point of impingement on a position-sensitive detector allows for determination of the lateral position of each ion on the tip, and enables a 3D reconstruction of the constituent atoms in the specimen.

A limiting factor for prior art APT analysis is the mechanical stress that is induced on the needle-shaped specimen, which arises from the high electric field. This issue has restricted the technique to analysis of relatively hard solid materials, such as metals, semiconductors and minerals. To date, no meaningful information about the structure of organic materials has been directly obtained using APT. The primary reason for this is the lack of mechanical strength and electrical conductivity of organics, precluding controlled evaporation of atoms from the surface.

The present invention solves the above mentioned shortcomings of APT by the fabrication of needle specimen tips with sufficient mechanical integrity to permit APT analysis of biomolecules with atomic resolution. This is possible by enclosing the biomolecules in an amorphous silica matrix, such as an amorphous, inorganic silica or silicate matrix or structure.

Accordingly, an aspect of the embodiments relates to a method for determining a 3D structure of a biomolecule. The method comprises, see FIG. 10, encapsulating the biomolecule in an amorphous silica matrix in step S1. The method also comprises preparing, in step S2, a needle specimen comprising the amorphous silica matrix. Atom probe tomography (APT) analysis is performed of the needle specimen in step S3 to determine the 3D structure of the biomolecule.

Thus, according to the present embodiments, the biomolecule is embedded in an amorphous silica matrix. This amorphous silica matrix effectively provides sufficient mechanical strength and integrity to allow fabrication of a needle specimen that can be used in the APT analysis.

The amorphous silica matrix not only enables fabrication of the needle specimen but additionally simplifies identification of carbon-containing biomolecules from background during the analysis. The reason being that the amorphous silica matrix typically does not contain any carbon that may interfere with the APT analysis of the biomolecule. This problem of distinguishing the relevant sample from the background is otherwise present in the art when using organic polymers to embed and encapsulate samples to be analyzed.

The needle specimen prepared or fabricated in step S2 has a general needle shape, i.e., a thin tip, which is adapted for APT analysis. The needle specimen could be a uniform needle-shaped specimen of the amorphous silica matrix encapsulating the biomolecule. It is, however, also possible to have a core structure onto which the amorphous silica matrix is deposited to form a needle-shaped specimen, which will be further described herein.

Examples of embodiments of the present invention are presented below. However, the present invention may be embodied in several ways, additional to and not limited by procedures or embodiments described herein.

Silica Embedding of Proteins

The present embodiments involve incorporation of biomolecules, such as proteins, protein fragments and peptides, in their native conformational state into an amorphous silica matrix.

Two different types of silica precursors have been used interchangeably for the syntheses of silica in the present invention. The first embodiment involves an organic route where an alkoxide, such as tetramethylorthosilicate, tetraethylorthosilicate, tetrapropylorthosilicate or tetrabutylorthosilicate, or any other alkoxide with the generic formula $Si(OR)_4$, where R is an alkyl chain, preferably a C1-C8 alkyl chain, or phenyl, is used as the silica precursor. The second embodiment involves an inorganic route, where sodium silicate (waterglass) is used as the silica precursor. Mixtures of inorganic and organic silica precursors may also be employed. Previous work have confirmed the preservation of proteins with retained structure and function after embedding in solid silica using both organic and inorganic silica precursors [1, 2]

Alkoxides spontaneously hydrolyze when introduced to water and condensate forming an inorganic amorphous network of silicon and oxygen. The reaction is dependent on the nature of the organic side chains, pH, ratio $H_2O$/alkoxide, and temperature. By varying these parameters, the gelling time and physical appearance of the formed solid can be controlled [3]. The hydrophobicity of alkoxides can be beneficial for certain preparations where penetration of the alkoxide into, for example, lipid bilayers or the hydrophobic core of larger molecules or biological structures can facilitate silicon dioxide deposition and, hence, the embedding of the biomolecule.

Figure 3:
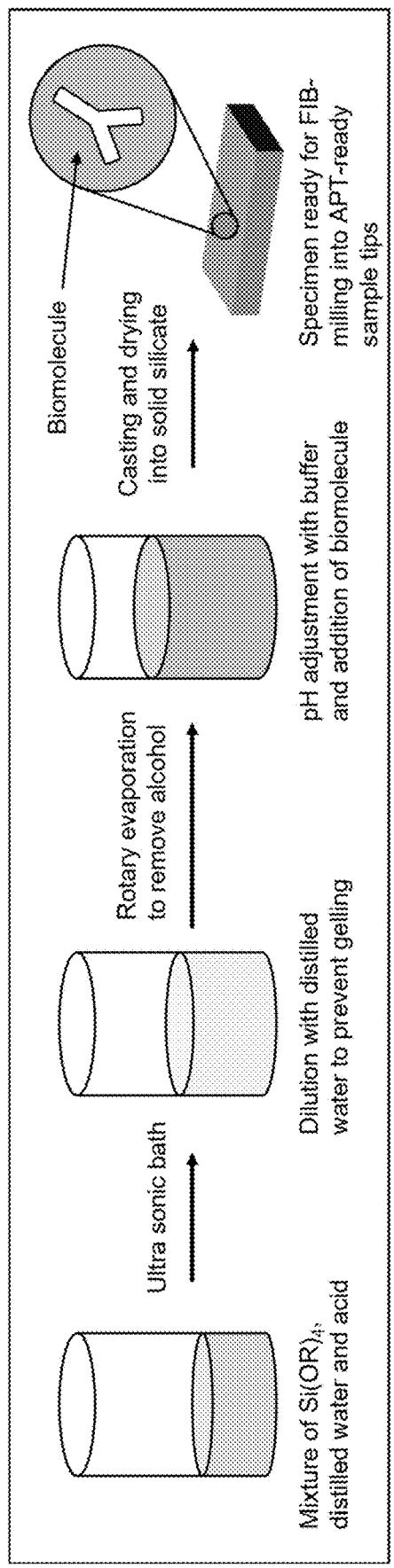
FIG. 3 shows an overview of the synthesis and fabrication of an APT specimen produced using an organic silica precursor as described in Example 1.

An overview of the procedure for biomolecule embedding into an amorphous silica matrix derived via an alkoxide route in the present invention is shown in FIG. 3. During hydrolysis of an alkoxide, alcohol is formed as a by-product. In order to avoid unfolding or denaturation of the biomolecule, the alcohol is preferably removed by, for example, rotary evaporation, leaving only an aqueous solution of silicic acid. To further ensure the stability of the biomolecule, the inherently low pH of the silicic acid solution is preferably adjusted to the individual physiological range of the biomolecule in question before the biomolecule is introduced into the silica solution.

Figure 5:
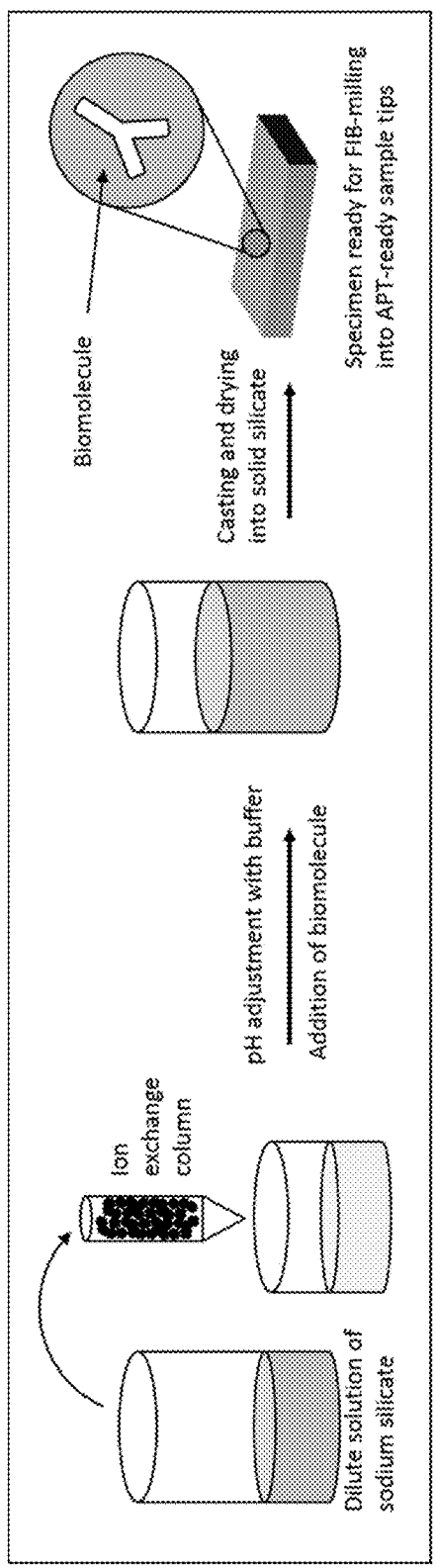
FIG. 5 shows an overview of the synthesis and fabrication of an APT specimen produced using an inorganic silica precursor as described in Example 2.

Aqueous sodium silicate solutions prepared from sodium silicates with the generic formula $Na_{2x}SiO_{2+x}$ or $(Na_2O)_x \cdot SiO_2$, such as sodium metasilicate ($Na_2SiO_3$), sodium orthosilicate ($Na_4SiO_4$), and sodium pyrosilicate ($Na_6Si_2O_7$), spontaneously form a solid glassy sodium silicate gel upon evaporation of water from the solution. The physical properties of the gel can be controlled by varying the gelling time, temperature, the ratio $SiO_2:Na_2O$ and addition of ionic species in the solution [4]. An example of the biomolecule embedding procedure used in the present invention is illustrated in FIG. 5. In contrast to the alkoxide route described above, aqueous sodium silicate solutions are alkaline and therefore not suitable for dissolving proteins without risk of compromising their 3D structure. However, by passage of the sodium silicate solution through an ion exchange column $Na^+$ ions in the sodium silicate solution is exchanged for $H^+$ ions from the acidic ion exchange gel, thereby lowering the pH. The final pH is then adjusted to a desired level by addition of a base/acid or buffer solution.

The use of aqueous sodium silicate solutions can be advantageous over organic precursors since it is does not form alcohols as by-products during the gelling. This can be beneficial if sensitive biomolecules are to be analyzed since alcohols are known to compromise the structural integrity of several proteins. Also, as alcohols are organic molecules any residues left in the formed silica may interfere with carbon emanating from the target biomolecule when analyzed in the atom probe.

Although sodium silicates are preferred inorganic silica precursors, the present invention is not limited thereto. Also other inorganic silicates can be used instead of or in combination with sodium silicates. Such other inorganic silicates comprise, but are not limited to, potassium silicates, ammonium silicates and magnesium silicates.

Using the above routes, biomolecules may be embedded in a bulk matrix of silica using various embodiments; either as individual molecules dispersed in the amorphous silica matrix, as pre-adsorbed on a substrate, incorporated or in situ in a supported lipid bilayer or incorporated in lipid mono- or bilayer vesicles.

Figure 10:
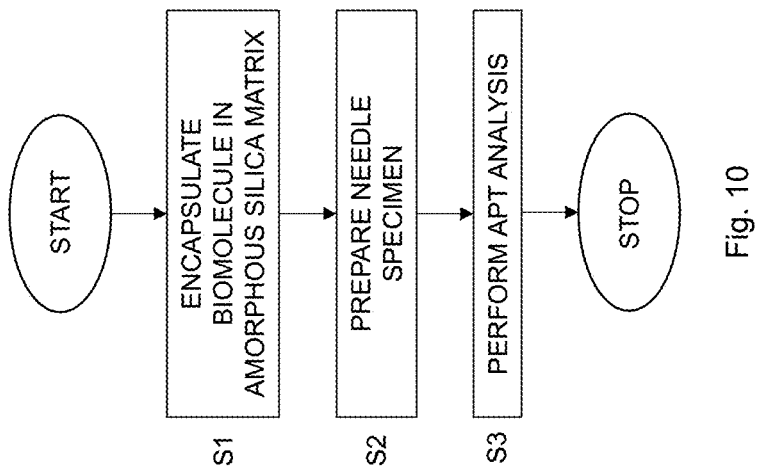
FIG. 10 is a flow chart illustrating a method for determining a 3D structure of a biomolecule.

Thus, in an embodiment step S1 of FIG. 10 comprises encapsulating the biomolecule in a sol-gel process producing a sol-gel from an organic silica precursor and/or an inorganic silica precursor. The sol-gel comprises the biomolecule.

In an embodiment, the organic silica precursor is an alkoxide having a general formula of $Si(OR)_4$. In a preferred embodiment, R is an alkyl or a phenyl. In a more preferred embodiment, R is a C1-C8 alkyl or phenyl, and more preferably a C1-C4 alkyl, or phenyl.

In a particular embodiment, the alkoxide is selected from a group consisting of tetramethylorthosilicate, tetraethylorthosilicate, tetrapropylorthosilicate, tetrebutylorthosilicate, and a mixture thereof.

In an embodiment, the inorganic silica precursor is a sodium silicate, preferably selected from a group consisting of $Na_{2x}SiO_{2+x}$, $(Na_2O)_x \cdot SiO_2$ and a mixture thereof. In this embodiment, x is a positive integer, preferably selected from the group consisting of 1, 2 and 3.

Figure 8:
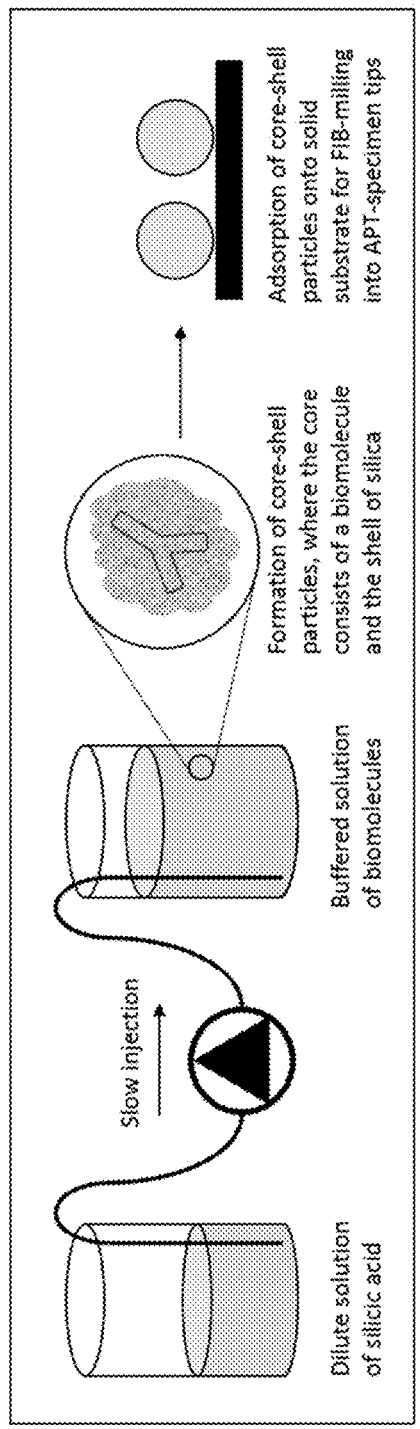
FIG. 8 is an overview of the synthesis of core-shell nanoparticles, where the core is comprised of a biomolecule and the shell is comprised of an amorphous silica matrix, as described in Example 4.

In addition to the above, biomolecules may be individually coated by a wrapping of in situ formed silicon dioxide to create core-shell nanoparticles where the core ideally consists of one single biomolecule and the shell consists of silica [5]. When the silica precursor is introduced through slow injection into the biomolecule solution the biomolecule surface acts as a condensation core for the polymerization of a silica network and a "shell" of solid silica is formed around the biomolecule. For the shell formation, silicic acid derived from an inorganic precursor, an organic precursor or a mixture of inorganic and organic precursors may be used. By using this approach, the problem of localizing individual biomolecules for APT analysis is circumvented since individual core shell particles are more easily detected and handled in the preparation of atom probe samples than individual molecules. A schematic over the synthesis of biomolecule containing core shell nanoparticles is shown in FIG. 8.

Thus, in an embodiment, step S1 of FIG. 10 comprises preparing core-shell particles comprising a core comprising the biomolecule and a shell of in situ formed silicon dioxide from an organic silica precursor and/or an inorganic silica precursor.

The organic and/or inorganic silica precursor used in the present embodiment can be selected from the alkoxide and sodium silicate examples presented above.

The encapsulation or embedding in step S1 is preferably performed at least partly based on information of the physico-chemical properties of each individual type of biomolecule to be analyzed. For instance, at least one of the pH and ionic strength of the silica solution can be adjusted in accordance with the charge of the biomolecule, hydrophilicity of the biomolecule, iso-electric point of the biomolecule, size of the biomolecule, and/or concentration of the biomolecule. Such an adjustment of the silica solution based on properties of the biomolecule prevents or at least significantly reduces the risk of aggregation or denaturation of the biomolecule. In addition, effective dispersion of the biomolecule in the amorphous silica matrix is ensured. The optimal concentration of biomolecule in the amorphous silica matrix is dependent on the molecular weight and of the chemical properties of the molecule in question and can be determined experimentally.

Specimen Preparation for Apt Analysis

Figure 2:
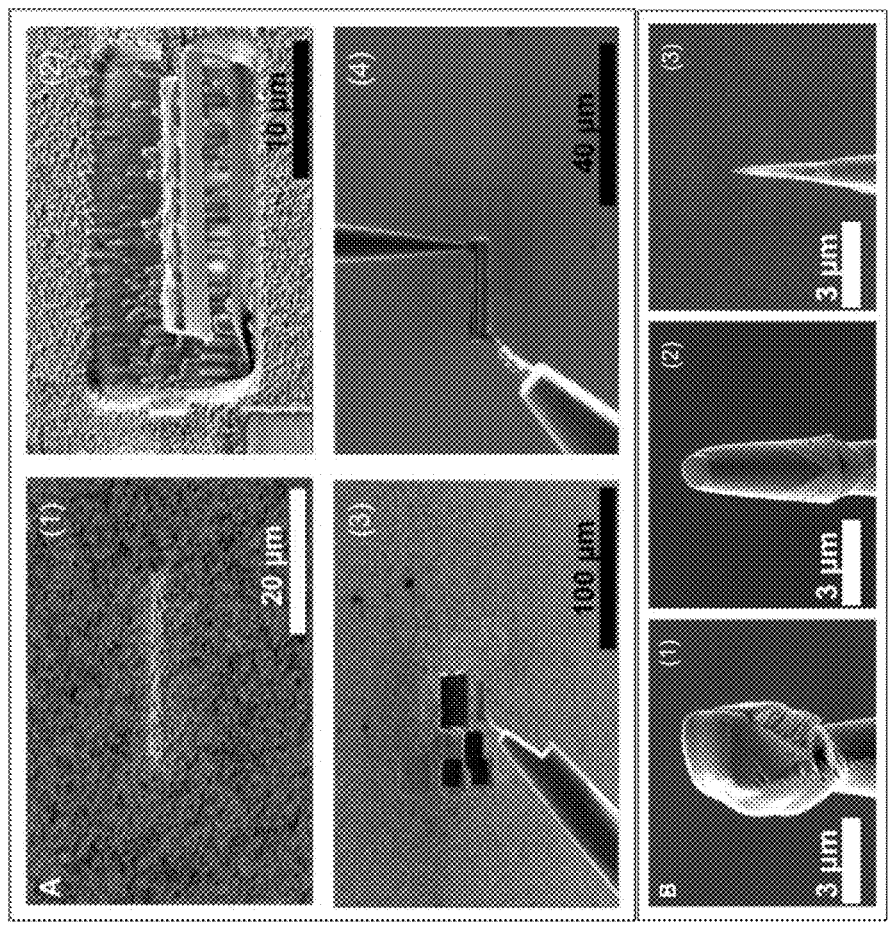
FIG. 2A are scanning electron microscope (SEM) micrographs illustrating a focused ion beam-scanning electron microscope (FIB-SEM) lift-out procedure (1-3) and subsequent attachment to silicon posts (4) for preparation of ultra-sharp specimen needles from an amorphous silica matrix.
FIG. 2B are SEM micrographs showing the annular milling procedure where a sharp tip suitable for APT analysis is produced.

APT analysis uses ultra-sharp needle specimens fabricated from the target material, i.e., the amorphous silica matrix according to the embodiments. For instance, the tip of the needle specimen preferably has a radius that is smaller than 100 nanometers. The fabrication of such sharp needle specimen in step S2 of FIG. 10 is preferably done using a combined focused ion beam-scanning electron microscope (FIB-SEM) procedure. Before insertion into the microscope, a protective metal layer is preferably sputtered onto the amorphous silica matrix surface to protect the region of interest from damage by the ion and electron beams, and enhance surface conductivity. For additional protection, a platinum (Pt) strip or rectangle of approximate dimensions 20×2 μm is preferably deposited on the surface inside the microscope. The stage is then tilted to an angle of, preferably, 22° and ion milling is performed on both sides of the Pt strip so as to form a wedge underneath. One end of the wedge is then cut free, and a micromanipulator needle is introduced and is attached to the freed end of the wedge by means of Pt deposition. Once attached, the other end of the wedge is cut free and the needle is retracted. A coupon with flat top silicon posts is then brought into the field-of-view. The wedge is brought into contact with the top of a conductive silicon post, and attached using Pt deposition. Once a piece of the wedge is secured to the silicon post, it is preferably sliced off from the rest of the wedge. This procedure is repeated until 3-10 pieces or segments of the wedge have been mounted on posts. Pt is then preferably deposited on the backside of each piece. Finally, using annular milling from above with decrementally smaller radii, a tip is produced. The milling is performed at smaller and smaller ion currents so that the apex is placed in the region of interest, i.e., in the amorphous silica matrix piece. An overview of the whole process from platinum deposition to a final APT ready sample tip is shown in FIGS. 2A and 2B.

In an embodiment, step S2 of FIG. 10 comprises performing a focused ion beam (FIB) milling on the amorphous silica matrix to form a needle tip comprising the amorphous silica matrix.

In a particular embodiment, the needle tip preferably has a radius that is smaller than 100 nm.

In an embodiment, performing the FIB milling comprises FIB milling the amorphous silica matrix to form a wedge of the amorphous silica matrix. The wedge is attached onto a micromanipulator needle. This embodiment also comprises mounting segments or pieces of the wedge on a conductive silicon post and FIB milling the segments or pieces to form the needle tip.

Figure 7:
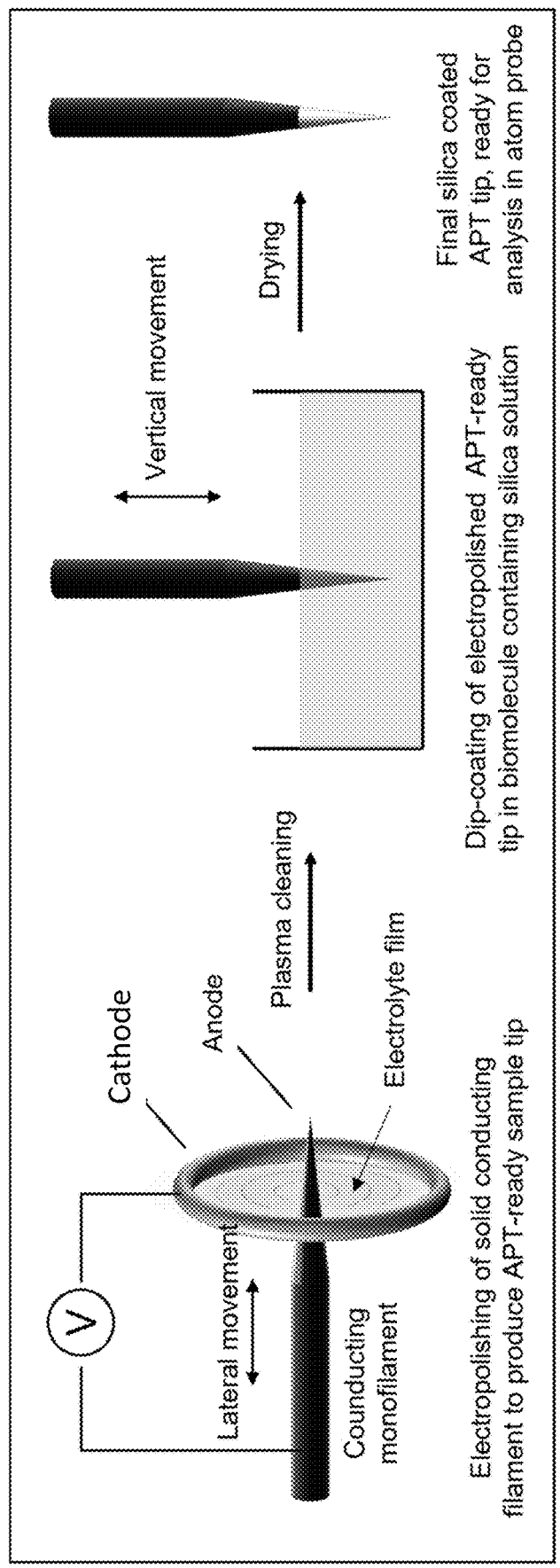
FIG. 7 depicts an overview of the preparation of silica coated APT sample tips prepared by electro-polishing and dip-coating of a conducting monofilament as described in Example 3.

In another embodiment, the needle specimen with a needle tip is obtained by coating a pre-fabricated needle tip with the amorphous silica matrix or depositing the amorphous silica matrix onto the pre-fabricated needle tip to form the needle tip. This embodiment is schematically illustrated in FIG. 7. Hence, in such an embodiment step S2 of FIG. 10 comprises coating a pre-fabricated needle tip with the amorphous silica matrix to form a needle tip comprising the amorphous silica matrix.

In a particular embodiment, the needle tip preferably has a radius that is smaller than 100 nm.

Adjusting parameters in the synthesis of the amorphous silica matrix to cohere with the physico-chemical properties of the target biomolecule will also have an effect on the mechanical strength and suitability of the final sample tip for analysis in the atom probe. For example, amorphous silica matrices with neutral pH was superior in mechanical strength when prepared from an inorganic silica source compared to a silica matrix derived from an organic silica source, such as tetraethyl orthosilicate (TEOS), due to low formation of pores in the inorganic-derived silica.

Hence, in an embodiment step S1 in FIG. 10 comprises encapsulating the biomolecule in a sol-gel process producing a sol-gel from an inorganic silica precursor. The sol-gel comprises the biomolecule and has a neutral pH, i.e., a pH around 7, such as a pH from 6.6 up to 7.3.

Atom Probe Tomography Analysis and Reconstruction

Laser-assisted APT analysis was performed using standard analysis conditions for oxides, when a green ($\lambda=532$ nm) laser was used. Field evaporation was initiated by laser pulsing at 200 kHz with a pulse energy of 0.5 nJ, at a nominal evaporation rate of 0.005 ions per pulse. If a UV laser-pulsed atom probe is used, the laser energy can be reduced to approximately 0.1 nJ. The temperature at the base of the tip was held at 50 K during analysis and the pressure in the analysis chamber was approximately $10^{-9}$ Pa. The detection efficiency of the instrument was approximately 37% during the experiments, and can be assumed to be indiscriminate over all ionic species in the spectra.

Reconstructions were performed using a standard protocol for APT, where a constant shank angle of the tip was assumed. The method has been described in detail by Geiser et al [6]. Shank angles can be estimated with good accuracy, by examining high-resolution scanning electron microscopy images of the tips prior to analysis. Alternatively, voltage-based reconstruction may be used to produce atomic tomograms, albeit with somewhat compromised precision [7].

Spatial distributions of the atomic constituents of the biomolecule were evaluated by dividing the analyzed volume into voxels. Atomic density distributions could then be deduced and visualized in the form of heat maps.

FIG. 1 is a flow chart summarizing different embodiments of the invention from the embedding of the biomolecule up to the APT analysis.

The present invention solves a problem with extensive protein sample preparation for X-ray diffraction (XRD) and risk of loss of protein structural integrity caused by purification or crystallization of the protein.

The present invention solves a problem with limitations in biomolecule size for analyses with NMR or TEM.

The present embodiment can be used to determine the 3D structure of any biomolecule that can be encapsulated in the amorphous silica matrix. Non-limiting, but illustrative examples, of such biomolecules include proteins, protein fragments and peptides, including enzymes and antibodies. The embodiments can be used both for membrane proteins, such as integrated membrane proteins and transmembrane proteins, and non-membrane or soluble proteins. The biomolecule may also be in the form of a complex of multiple proteins, protein fragments and/or peptides, or a complex between protein(s), protein fragment(s), peptide(s) and other biomolecules, such as nucleic acid molecules, carbohydrates, lipids, etc.

Other examples of biomolecules include lipids and nucleic acid molecules, such as DNA and/or RNA molecules.

EXAMPLES

Example 1

Preparation of Atom Probe Samples Using an Organic Silica Precursor

Figure 4:
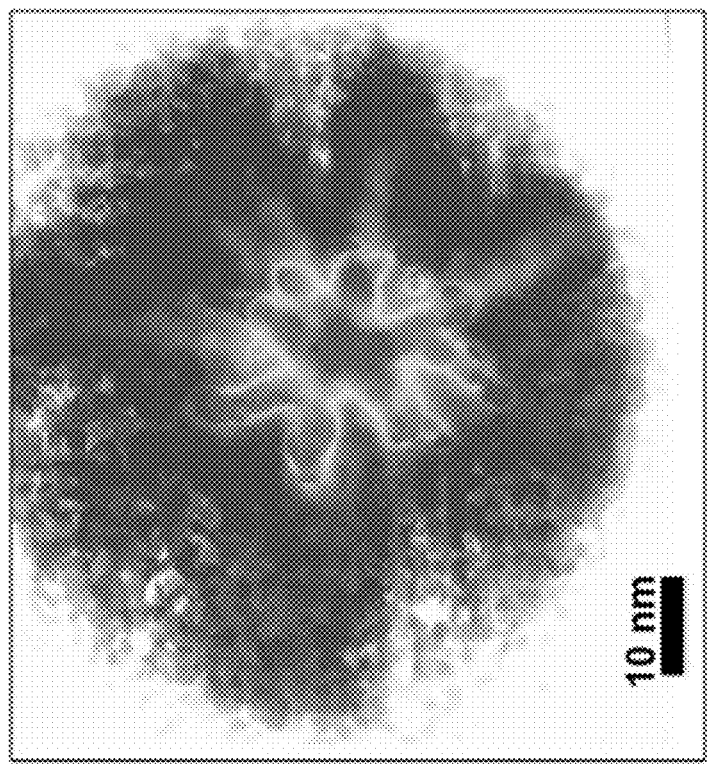
FIG. 4 depicts an atomic density heat map from an APT reconstruction of an aggregate of IgG molecules embedded in an amorphous silica matrix derived from an organic silica precursor.

For protein embedding using an organic silica precursor, a mixture of 2 ml TEOS, 972 µl water and 61 µl HCl (0.1 M) was sonicated in an ultrasonic bath for 60 minutes after which an additional 4 ml of milliQ water was added to prevent immediate gelling. The ethanol formed during the hydrolysis reaction was then removed using a rotary evaporator to avoid damage from the ethanol to the structural integrity of the proteins. To this flask 60 µl of immunoglobulin G (IgG) (10 mg/ml in 10 mM Sorensen's phosphate buffer) was added under stirring. The solution was then incubated at 37° C. in ambient atmosphere as droplets (30 µl) on a standard microscope glass slide or as larger volumes in vials to produce a bulk material. APT specimen needles were then prepared from the formed protein containing silica material using FIB-SEM as described above. A schematic of the procedure is shown in FIG. 3 and an example of APT data acquired from the above synthesis is shown in FIG. 4.

Example 2

Preparation of Atom Probe Samples Using an Inorganic Silica Precursor

Figure 6:
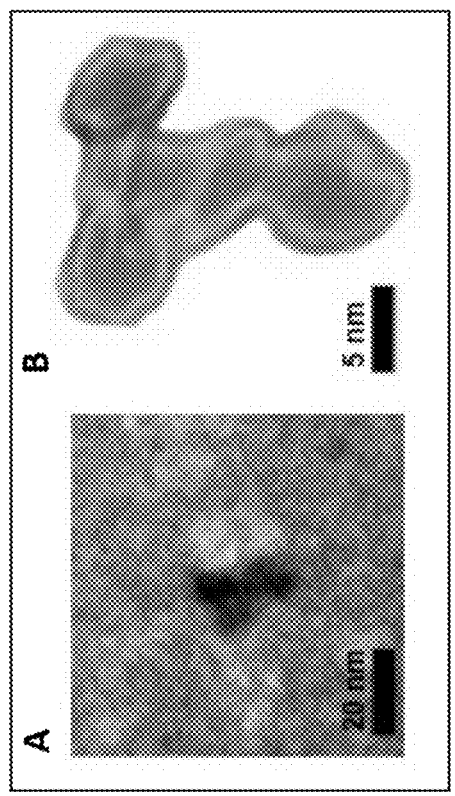
FIG. 6A depicts a TEM micrograph of an individual IgG molecule embedded in an amorphous silica matrix derived from an inorganic silica source as described in Example 2.
FIG. 6B is a 3D atomic density heat map from an APT reconstruction of a single IgG molecule embedded in an amorphous silica matrix as described in Example 2.

A commercial available sodium silicate solution (Sigma) containing 26.5% $SiO_2$ was used as the source for inorganic silica. After dilution to ~9% in milliQ-water, the pH was adjusted to physiological values by passing the solution through an acidic ion exchange gel column. 50 µl of a buffer containing 3.8 mg/ml of immunoglobulin G (IgG) in 10 mM phosphate-buffered saline (PBS) was added to 100 µl of the diluted silica solution under stirring. The solution was then incubated at 37° C. in ambient atmosphere as droplets (20 µl) on a standard microscope glass slide or as larger volumes in vials to produce a bulk material. The procedure is schematically shown in FIG. 5. APT specimen needles were then prepared from the protein containing silica using FIB-SEM as described above and then analyzed using atom probe tomography. In FIG. 6A, a TEM micrograph of a single IgG molecule embedded in a solid silica matrix using the above preparation technique is shown. FIG. 6B shows a reconstruction of an IgG molecule using data acquired from APT analysis of a single IgG molecule embedded in a solid silica matrix prepared using the same protocol.

Example 3

Preparation of Atom Probe Samples by Coating of a Pre-Fabricated Atom Probe Tip

A tungsten tip with suitable dimensions for atom probe analysis (radius<100 nm) was fabricated from a tungsten wire (diameter 0.1 mm) through electro polishing. A 10 mm wire segment was mounted in an aluminum holder to fit in the atom probe instrument. The end of the segment was repeatedly moved in and out of an electrolyte-covered gold loop, to which a 5 V AC was applied. The procedure was stopped when a sufficiently sharp (radius<100 nm) tip was formed. The tungsten needle was cleaned in an argon plasma chamber for 15 min before the coating procedure. A solution of silicic acid was prepared through any of the two methods described in Example 1 and Example 2. A buffered solution (PBS, 10 mM) containing 10 mg/ml fluorescein isothiocyanate (FITC) labelled rabbit anti-human IgG (Sigma) was mixed with the silicic acid solution and the apex of the pre-fabricated tip was dipped into the protein containing silica solution and immediately retracted and left to dry in ambient air for 24 h before analysis. The samples were examined with fluorescence microscopy to confirm the presence of the protein coating, and in SEM to assure suitable dimensions of the tip before atom probe tomography analysis. An illustration of the procedure is provided in FIG. 7.

Example 4

Preparation of Atom Probe Samples Using Biomolecule-Core-Shell Silica Particles

Core shell particles bearing a biomolecule core was prepared by slow injection (1 ml/h) of 250 µl of a solution of silicic acid (10 mM) prepared through any of the methods above, into 250 µl of a buffered solution (Sorensen's phosphate buffer 10 mM) of IgG (final concentration of IgG was 50 nm). To immobilize the synthesized core shell particles on a solid support, a silicon wafer was cleaned with basic piranha solution (5:1:1 ratios of $H_2O:NH_3:H_2O_2$) and functionalized with 2% aminopropyl triethoxysilane (APTMS) in anhydrous toluene. The particles were then immobilized on the silicon wafer by immersing the wafer into a solution of the aforementioned particles for 60 min. The wafer was then rinsed with MilliQ water and dried under a gentle stream of gaseous nitrogen. Lift-outs and preparation of APT specimen needles of the immobilized particles were then performed using a focused ion beam-SEM as previously described. An illustration of the procedure is provided in FIG. 8.

Example 5

Figure 9:
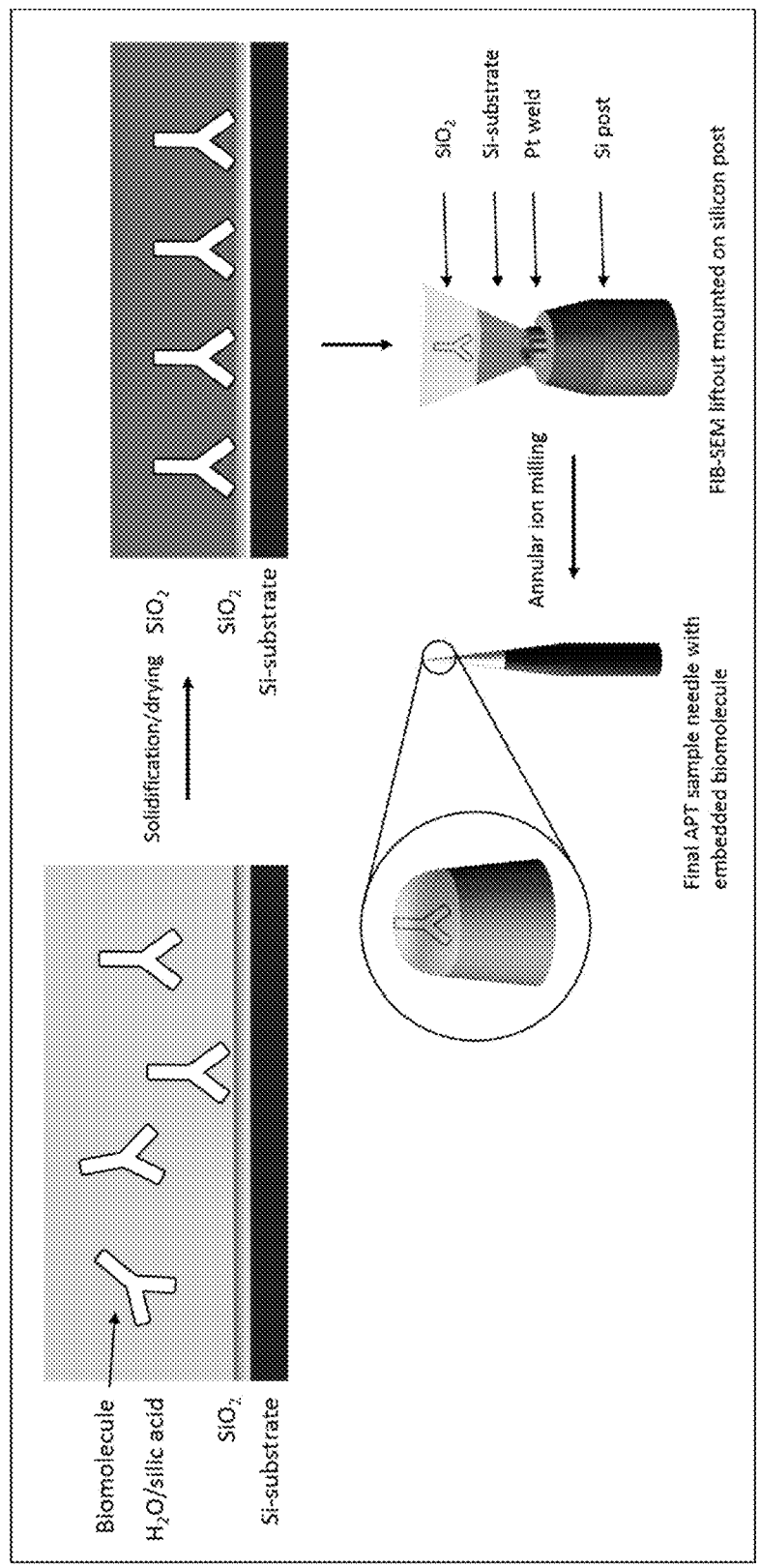
FIG. 9 depicts the process described in Example 5 where biomolecules are immobilized onto a solid support and subsequently embedded in an amorphous silica matrix from which a FIB-SEM lift-out is performed, followed by annular ion milling to produce needle shaped specimen for APT analysis.

Preparation of Atom Probe Samples from Silica-Embedded Surface Adsorbed Biomolecules APT analyses have larger probability of success if the needle-shaped samples are conducting, allowing the electrical potential to propagate to the apex of the tip. In order to minimize the amount of dielectric material, i.e., silica, in the needle, a specialized sample preparation procedure was devised. This method had the added benefit of providing a target during the FIB-SEM tip preparation step, as the biomolecules were immobilized near an interface that gave high contrast when imaged with the electron beam. In this example, a silicon wafer was furnished with a thin silicon oxide layer through washing in basic piranha and washed thoroughly with distilled water. The wafer was subsequently immersed in a buffered solution of IgG (500 µg/ml) for 1 h, to allow for adsorption of proteins on the surface. Unbound proteins were then washed away with distilled water and silicic acid (total concentration 1.7% v/v) was mixed into the solution, forming an amorphous silica matrix surrounding the protein layer. The wafer was rinsed with distilled water after 18 h and dried with gaseous nitrogen. The top surface of the wafer was sputtered with a 10 nm Pd coating layer to enhance conductivity, and liftouts were performed as described above. The protein-containing region of the tip could be targeted with the FIB-SEM as the Si—$SiO_2$ interface gave a sharp contrast using electron beam imaging. Milling was stopped approximately 50 nm above the Si segment of the needle, with the apex encompassing the protein layer. In addition to embedding surface adsorbed proteins, the above procedure may also be applied to embed supported protein-containing lipid bilayers, or lipid mono- or bilayer vesicles adsorbed on a solid support for atom probe analyses of membrane associated proteins. A schematic of the procedure is shown in FIG. 9.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1]. Luckarift, H. R., et al., *Enzyme immobilization in a biomimetic silica support*. Nat Biotech, 2004. 22(2): p. 211-213.
2. Bhatia, R. B., et al., *Aqueous Sol-Gel Process for Protein Encapsulation*. Chemistry of Materials, 2000. 12(8): p. 2434-2441.
3. Brinker, C. J., *Hydrolysis and condensation of silicates: Effects on structure*. Journal of Non-Crystalline Solids, 1988. 100(1): p. 31-50.
4. Coradin, T. and P. J. Lopez, *Biogenic silica patterning: Simple chemistry or subtle biology?* Chembiochem, 2003. 4(4): p. 251-259.
5. Jackson, E., et al., *Protein-Templated Biomimetic Silica Nanoparticles*. Langmuir, 2015. 31(12): p. 3687-3695.
6. Geiser, B. P., et al., *Wide-Field-of-View Atom Probe Reconstruction*. Microscopy and Microanalysis, 2009. 15(S2): p. 292-293.

7. Bas, P., et al., *A general protocol for the reconstruction of 3D atom probe data*. Applied Surface Science, 1995. 87: p. 298-304.

The invention claimed is:

1. A method for determining a three dimensional (3D) structure of a biomolecule, said method comprising:
   preparing (S1) an amorphous silica matrix that encapsulates said biomolecule;
   preparing (S2) a needle specimen comprising said amorphous silica matrix that encapsulates said biomolecule; and
   performing (S3) atom probe tomography analysis of said needle specimen to determine said 3D structure of said biomolecule,
   wherein preparing (S1) said amorphous silica matrix comprises encapsulating said biomolecule via a sol-gel process that uses an organic precursor to silica and/or an inorganic precursor to silica.

2. The method according to claim 1, wherein preparing (S1) said amorphous silica matrix that encapsulates said biomolecule comprises preparing core-shell particles comprising a core comprising said biomolecule and a shell of in situ formed silicon dioxide from an organic precursor to silica and/or an inorganic precursor to silica.

3. The method according to claim 1, wherein said organic precursor to silica has a general formula of $Si(OR)_4$, wherein R is an alkyl or phenyl.

4. The method according to claim 3, wherein R is a C1-C8 alkyl or phenyl.

5. The method according to claim 4, wherein R is a C1-C4 alkyl or phenyl.

6. The method according to claim 5, wherein said organic precursor to silica is selected from a group consisting of tetramethylorthosilicate, tetraethylorthosilicate, tetrapropylorthosilicate, tetrabutylorthosilicate, and a mixture thereof.

7. The method according to claim 1, wherein said inorganic precursor to silica is a sodium silicate selected from a group consisting of $Na_{2x}SiO_{2+x}$ and $(Na_2O)_x.SiO_2$, wherein x is a positive integer selected from a group consisting of 1 and 2.

8. The method according to claim 7, wherein x is 1.

9. The method according to claim 1, wherein preparing (S2) said needle specimen comprises performing a focused ion beam (FIB) milling on said amorphous silica matrix that encapsulates said biomolecule to form a needle tip comprising said amorphous silica matrix.

10. The method according to claim 9, wherein performing FIB milling comprises:
   FIB milling said amorphous silica matrix that encapsulates said biomolecule to form a wedge of said amorphous silica matrix;
   attaching said wedge onto a micromanipulator needle;
   mounting segments of said wedge on a conductive post; and
   FIB milling said segments to form said needle tip.

11. The method according to claim 9, wherein said needle tip has a radius that is smaller than 100 nm.

12. The method according to claim 1, wherein preparing (S2) said needle specimen comprising said amorphous silica matrix that encapsulates said biomolecule comprises coating a pre-fabricated needle tip with a solution comprising said biomolecule and said organic precursor to silica and/or said inorganic precursor to silica.

13. The method according to claim 1, wherein said biomolecule is selected from a group consisting of a protein, a protein fragment and a peptide.

\* \* \* \* \*

UNITED STATES PATENT AND TRADEMARK OFFICE
CERTIFICATE OF CORRECTION

PATENT NO. : 11,714,091 B2
APPLICATION NO. : 16/629166
DATED : August 1, 2023
INVENTOR(S) : Andersson et al.

It is certified that error appears in the above-identified patent and that said Letters Patent is hereby corrected as shown below:

In the Specification

Column 1, Line 62: Please correct "Angstrom" to read --Ångström--

Column 1, Line 63: Please correct "-300" to read --~300--

Column 5, Line 5: Please correct "$(Na_2O)_x.SiO_2$" to read --$(Na_2O)_x \cdot SiO_2$--

Column 5, Line 59: Please correct "$(Na_2O)_x.SiO_2$" to read --$(Na_2O)_x \cdot SiO_2$--

Column 8, Line 63: Please correct "-9%" to read --~9%--

Column 10, Line 51: Please correct "[1]." to read --1.--

In the Claims

Column 12, Line 5, Claim 7: Please correct "$(Na_2O)_x.SiO_2$" to read --$(Na_2O)_x \cdot SiO_2$--

Signed and Sealed this
Fourteenth Day of November, 2023

*Katherine Kelly Vidal*

Katherine Kelly Vidal
*Director of the United States Patent and Trademark Office*